(12) United States Patent
Chtourou

(10) Patent No.: US 8,383,104 B2
(45) Date of Patent: Feb. 26, 2013

(54) THROMBIN-FREE BIOLOGICAL ADHESIVE AND USE THEREOF AS A MEDICAMENT

(75) Inventor: Abdessatar Chtourou, Elancourt (FR)

(73) Assignee: Laboratoire Francais du Fractionnement et des Biotechnologies S.A., Les Ulis (FR)

( * ) Notice: Subject to any disclaimer, the term of this patent is extended or adjusted under 35 U.S.C. 154(b) by 58 days.

(21) Appl. No.: 12/096,883

(22) PCT Filed: Dec. 15, 2006

(86) PCT No.: PCT/FR2006/002747

§ 371 (c)(1),
(2), (4) Date: Aug. 26, 2008

(87) PCT Pub. No.: WO2007/080276

PCT Pub. Date: Jul. 19, 2007

(65) Prior Publication Data

US 2008/0311190 A1   Dec. 18, 2008

(30) Foreign Application Priority Data

Dec. 16, 2005   (FR) ..................... 05 12817

(51) Int. Cl.
  A61K 38/48   (2006.01)
  A61K 9/66    (2006.01)
  A61K 9/64    (2006.01)
  A61F 13/00   (2006.01)
  A61L 15/16   (2006.01)

(52) U.S. Cl. .............. 424/94.64; 424/443; 424/444; 424/455; 424/456

(58) Field of Classification Search ............... 424/94.64, 424/443, 444, 455, 456
See application file for complete search history.

(56) References Cited

U.S. PATENT DOCUMENTS

| | | | |
|---|---|---|---|
| 4,377,572 | A | 3/1983 | Schwarz et al. |
| 4,414,976 | A | 11/1983 | Schwarz et al. |
| 5,399,670 | A | 3/1995 | Bhattacharya et al. |
| 5,985,315 | A | 11/1999 | Patat et al. |
| 6,500,427 | B1 | 12/2002 | Heimburger et al. |
| 2006/0247426 | A1 | 11/2006 | Bardat |

FOREIGN PATENT DOCUMENTS

| | | |
|---|---|---|
| EP | 0305243 A1 | 3/1989 |
| EP | 0346241 A1 | 12/1989 |
| EP | 0850650 A1 | 1/1998 |
| FR | 2448900 A1 | 9/1980 |
| FR | 2448901 A1 | 9/1980 |
| FR | 2857267 A1 | 1/2005 |
| FR | 2866890 A1 | 9/2005 |
| FR | 2887883 A1 | 1/2007 |
| JP | 02167234 A | 6/1990 |
| JP | 1995-500095 | 7/1995 |
| JP | 2000-505714 | 5/2000 |
| JP | 2002-513645 | 5/2002 |
| JP | 2002-514948 | 5/2002 |
| WO | 93/06855 | 4/1993 |
| WO | 9306855 A1 | 4/1993 |
| WO | 97/29792 | 8/1997 |
| WO | 9729792 A1 | 8/1997 |
| WO | 98/29144 | 9/1998 |
| WO | 9915121 A | 4/1999 |
| WO | 99/56798 | 11/1999 |
| WO | 02055102 A | 7/2002 |
| WO | 2005004901 | 1/2005 |

*Primary Examiner* — Ganapathirama Raghu
(74) *Attorney, Agent, or Firm* — Marsh Fischmann & Breyfogle LLP

(57) ABSTRACT

The invention relates to a thrombin-free, fibrinogen-based biological adhesive for therapeutic use, which comprises factor VIIa and a source of calcium ions. The invention also relates to the use of the biological adhesive as a medicament, in particular as a dressing for biological tissues, wounds or biomaterials.

22 Claims, No Drawings

THROMBIN-FREE BIOLOGICAL ADHESIVE AND USE THEREOF AS A MEDICAMENT

The present invention relates to a fibrinogen-based biological adhesive with an activated factor VII and a source of calcium ions.

By "biological adhesive" is meant a component capable of joining tissue elements (skin, bone, various organs) and in the same time providing haemostasis of the damaged tissues, which may thus reinforce or complete joining of these tissues by suture(s).

Blood coagulation is achieved according to steps in cascade involving different proenzymes and procofactors present in blood which are converted via proteolytic enzymes into their activated form. This succession of coagulation steps or cascade is carried out according to two coagulation systems, called the extrinsic coagulation route and the intrinsic coagulation route, leading to transformation of prothrombin into thrombin.

The extrinsic route involves the intervention of the factor VII present in blood. However, the latter requires an activation (factor VIIa) for initiating this coagulation cascade. The factor VIIa has low enzymatic activity until it is complexed with tissue factors of phospholipid nature released after tissular damage. The thereby complexed factor VIIa transforms the factor X (FX) into the factor Xa (FXa) in the presence of calcium ions. The factor Xa in turn transforms prothrombin into thrombin, which activates the factor V (factor Va). Thrombin also activates the factor XIII (factor XIIIa). Thrombin, in the presence of calcium, tissular factors, factor Va, acts on fibrinogen by transforming it into fibrin. The presence of factor XIIIa allows formation of a clot of fibrin with a solid and adherent meshed network which is gradually and slowly resorbed with the setting up of the consolidation scar tissue, at which the network is used as a frame. This cross-linked fibrin is insoluble and cannot be attacked by fibrinolytic enzymes, at least during the time for setting up the scar tissue.

The intrinsic coagulation route also involves the factor VIIa (FVIIa). This route comprises a cascade of reactions resulting in the activation of thrombin via the factor XII (FXII). The latter activates the factor XI (factor XIa-FXIa) which activates the factor IX (factor IXa-FIXa) in the presence of phospholipid tissular factors (FT). The factor IXa participates in the activation of factor X into a factor Xa in the presence of the factor VIIIa, of tissue factors and of calcium ions. This then leads to transformation of prothrombin into thrombin. It should be noted that the presence of the factor Xa or thrombin allows activation of the factor VII (factor VIIa).

It therefore appears that the factor XIIa plays a prominent role in the mechanisms of intrinsic coagulation, resulting in the formation of a blood clot. It is used in treating haemophiliacs A having a circulating inhibitor, i.e. a specific antibody which limits or prevents activation of the factor VIII (FVIII). The factor VIIa has the advantage of being able to act locally in the presence of tissular factors released after lesion of tissues causing haemorrhages, even in the absence of the factor VIII or IX.

However, in the case of haemorrhagic tissular lesions caused by wounds, injuries or external surgical operations, tissue repair by suture is a requirement, notably for stopping haemorrhage by forming a fibrin clot, according to the mechanisms explained earlier. It may prove to be necessary to promote haemostasis of damaged tissues, notably in the case of severe surgical operations.

As an example, Patent Application WO 93/06855 may be mentioned, which describes a haemostatic composition, free of thrombin and of coagulation factors, comprising the factor VIIa incorporated into a biologically compatible vehicle, the whole being applied on a haemorrhagic injury in order to promote haemostasis and formation of a fibrin clot.

However, except for haemostasis of damaged tissues, the natural process for healing tissue, either sutured or not, related to joining tissues in order to avoid their impairment and accelerate the process, should also be accelerated, reinforced or even completed. This is notably possible by locally applying a biological adhesive.

Biological adhesives consist of a mixture of circulating factors of blood coagulation, notably of fibrinogenic plasma proteins and of the factor XIII. They further require a supply of exogenous thrombin, an enzyme necessary for transforming fibrinogen into insoluble fibrin, which may be cross-linked by the factor XIII. Additional components are required for carrying out coagulation of fibrinogen, notably the calcium ion, as $CaCl_2$, and possibly aprotinin, added for its anti-fibrinolytic properties.

Such biological adhesives were in particular described in different publications and patents, such as EP 0 305 243, FR 2 448 900 and FR 2 448 901, as well as their applications in miscellaneous clinical situations ("Fibrinkleber", Proceedings of the Heidelberg Congress, 1976, Ed. Schattauer).

Biological adhesives may also be used for binding biomaterials of miscellaneous nature (collagen, alginates, and polylactic acid) to biological tissues in order to reinforce their mechanical properties while waiting for consolidation by natural regrowth of the cells of the organism, for example artificial skin.

Commercially available biological adhesives in reality appear as kits comprising at least the four components mentioned above in a dry form, in which the proteins which may be coagulated by thrombin, fibrinogen and the factor XIII, should be isolated from thrombin, because their association causes solidification in fibrin within a very short time, of the order of a few seconds after reconstitution in a liquid and mixing. This is the reason why biological adhesive kits are provided with at least two components, i.e. comprising a batch based on fibrinogen and on factor XIII on the one hand and a batch based on thrombin on the other hand. The biological adhesive fulfils its functions indicated above by reconstitution and mixing of both batches, for example with syringes and needles, and then by application on the tissue to be sutured.

However, such reconstitutions and mixtures are relatively complex and a source of possible errors, notably in the case of an emergency, given the fact that as soon as fibrinogen is in contact with thrombin as a liquid, in the presence of other components, fibrin is formed almost instantaneously. Therefore the mixing of fibrinogen-thrombin may only be performed just before application on the wound or operating area. Further, when a single device for dispensing biological adhesive is used, there is an actual risk of solidification of fibrin in the actual device, which may lead to blocking of the dispensing and application system.

Patent EP 0 850 650 B1 notably describes a pre-activated two-component adhesive containing fibrinogen and at least one activated coagulation factor, the activation of which does not depend on calcium ions, selected from the Factor XIIa, the Factor XIa, the Factor VIIa and kallicrein and it coagulates by simple addition of calcium ions, by forming fibrin. This adhesive is obtained by fractionating or concentrating activated blood plasma from a single donor, in order to concentrate fibrinogen while retaining the activated coagulation factors required for allowing coagulation under the action of calcium ions. Such an adhesive has the drawbacks of the aforementioned two-component adhesives and of forming the fibrin clot upon mixing quasi-instantaneously.

Patent Application WO 02/055102 A1 describes a composition comprising FVIIa and fibrinogen useful for limiting or stopping bleeding caused by haemorrhages or internal or external injuries. These compositions are intended to be injected intravenously to the patient and they act at the haemorrhage or the injury where all the factors and the calcium ions are present. The drawback related to the use of such a composition lies in the fact that the latter interacts with the FTs which would have spread out of the injury or the haemorrhage, through the blood stream for example, and may cause with the calcium ions naturally present in blood, an untimely coagulation with the different factors present in the blood, causing clots out of the haemorrhagic area, with risks of thromboses.

The aforementioned drawbacks therefore pose problems in particular within the scope of surgical operations and/or urgency situations, where rapidity of the operating gesture is often a necessity. It is observed that such drawbacks are capable of generating an inhomogeneous joining of the tissues by formation of fibrin clusters before tissue adhesion, which may further be enhanced by retraction of the clot, finally leading to an irregular scar, favourable to deshience (disjoining of both banks of a scar) and to post-operating secondary bleedings.

In order to remedy these drawbacks, the Applicant sought to develop a biological adhesive meeting a dual related goal. The first goal is to provide a thrombin-free biological adhesive comprising plasma coagulation factors without the risk of forming fibrin before application on the biological tissue. The second goal meets the need of making such an adhesive available, also having increased capabilities of haemostasis of damaged tissues on the one hand and of joining tissues leading to enhanced healing on the other hand.

The invention relates to a stable thrombin-free fibrinogen-based single-compound liquid biological adhesive for therapeutic use, comprising the Factor VIIa and a source of calcium ions.

The Applicant found that it is possible to make a new medicament available (a single-compound biological adhesive): a haemostasis adjuvant, a dressing, a heeling adjuvant or sealing-off agent by formation of emboli, for biological tissues, wounds or biomaterials, comprising both above plasma factors of interest and a source of calcium ions.

By "single-compound", is meant a joint use of the three components of interest, constitutive of the adhesive thereby forming a single liquid compound, as opposed to two-component adhesives of the prior art.

These three components are therefore compatible with each other as a liquid, i.e. their combination, thereby forming a single-compound system, does not cause quasi-instantaneous formation of fibrin. This single-compound liquid adhesive is stable because these components may be in the presence of each other in a liquid medium for a functional use of the latter and this even at least for 24 hours before this use, without the risk of premature triggering of the coagulation process. This stability of the adhesive is verified, to the extent that no formation of fibrin is observed during 24 hours of incubation at 37° C.

The biological adhesive of the invention fulfils its repairing function for tissues once it is applied at the wound or the cruentous tissue because thrombin is formed in situ by contact of the biological adhesive on the wound or cruentous tissue.

Indeed, this in situ thrombin formation is provided by the Factor VIIa which is therefore put into contact with all the plasma components allowing triggering and progression of the extrinsic or intrinsic coagulation route. As explained earlier, its biological activity is dependent on the interaction with the endogenous tissular factors of phospholipid nature. The activated Factor VII tissular factors complex in the presence of calcium ions transforms the factor X present in the plasma into an activated factor X, which transforms prothrombin into thrombin, an enzyme responsible for forming the clot by generating fibrin in the presence of fibrinogen.

Formation of fibrin then occurs and consequently the adhesiveness of the obtained biological adhesive is reinforced, because fibrin then forms directly at the wound or tissue to be repaired by surgery, where the phospholipid cell components are exposed.

Although fibrinogen and calcium ions are already present naturally in blood, with their contribution, it is possible to reinforce and further accelerate even more the tissue joining and haemostasis process by the biological adhesive of the invention and this even when compared with the adhesives of the prior art. This is a decisive advantage of the present adhesive.

The biological adhesive of the invention has many other advantages. Its availability avoids drawbacks in handling and preparing biological adhesives of the prior art, notably in the case of emergency situations, which improves its capabilities in tissue adhesive bonding, in terms of deshience and absence of secondary bleedings at the scar in formation. Typically, the joining process may be achieved effectively in less than one minute, for example within 30 s.

As an example, the adhesive of the invention avoids the formation of "lumps" or clusters of fibrin visible at a wound which would be explained by inhomogeneous setting of the adhesive, probably because of the fibrin formed before adhesion, the formed scar further having a clear line, as compared with an adhesive bond of equal duration obtained for example by using a two-component biological adhesive based on a mixture of fibrinogen and containing the factor XIII, on the one hand, and a calcium thrombin mixture on the other hand, for which the above effects are not observed.

It is simple to prepare and has increased time stability, insofar that no formation of fibrin is observed for 24 hours of incubation at 37° C. As an example, it is therefore stable as a liquid for at least 24 hours at room temperature, in particular 48 hours.

Within the scope of the invention, any fibrinogen and FVIIa of the prior art, preferably plasmatic, are suitable for making the adhesive, however provided that they are compatible with the calcium ions of the thereby obtained adhesive as a liquid, i.e. their contacting does not cause coagulation of fibrinogen into fibrin, notably 24 hours before use. Indeed, both active ingredients, fibrinogen and FVIIa, should therefore be lacking, in addition to a lack of residual thrombin (FIIa), in coagulation factors such that, in the presence of calcium ions, the intrinsic or extrinsic coagulation cascade is triggered. Such coagulation factors represent the factor II (FII) and FX, and preferably the prothrombinic factors (factors II, VII, IX and X).

As an example, a maximum acceptable FII and FX content in fibrinogen is about 0.1 IU/g of fibrinogen for each of them.

Preferably, fibrinogen and FVIIa of the adhesive do not stem from pre-activated plasma.

Fibrinogen, preferably virally secure, may be isolated from plasma by any method developed in the prior art. It may be the method described in EP 0 305 243 or even the one developed by the Applicant in Patent Application FR 05 06640 according to which a fibrinogen concentrate may be obtained. Transgenic fibrinogen may also be implemented.

The factor XIII, preferably virally secure, may be isolated from plasma by any method developed in the prior art and it may advantageously form the protein which accompanies fibrinogen during fractionation of plasma. In this case, application of the method described in Patent Application FR 05 06640 is preferred. Transgenic factor XIII may also be implemented.

The preparation of the factor VIIa, notably as a concentrate, preferably virally secure, is also known. As an example Patent EP 346 241 may be mentioned. A recombinant (from Novo) or transgenic factor VIIa may also be used.

These active ingredients should however meet certain criteria of purity, as stated earlier, relating to the presence of notably certain other plasma factors.

Preferably, the adhesive of the invention further comprises the factor XIII. An exogenous supply of factor XIII promotes cross-linking of the fibrin network, and consequently, its coagulating power and healing potential.

The factor XIII, in particular as a concentrate, preferably virally secure, may be isolated from plasma by any method developed in the prior art and it may advantageously form the protein which accompanies fibrinogen during fractionation of the plasma. In this case, the method described in Patent Application FR 05 06640 is preferably applied. Transgenic factor XIII may also be implemented.

The adhesive of the invention may be made on an industrial scale by making two active ingredients available, fibrinogen and FVIIa, and calcium ions.

Preferably, the present adhesive consists of the sole mixture of fibrinogen, FVIIa and calcium ions. Such an adhesive exclusively consisting of these three components has the advantage of only requiring two biologically active ingredients, which notably limits the costs for preparing the adhesive on an industrial scale by the presence of a minimum but effective number of active components.

The constitutive components of the adhesive are present in effective amounts so that the adhesive may meet sought therapeutic goals.

The Applicant however observed that best results in terms of the aforementioned sought-after effects may be obtained when the contents of both active ingredients and of calcium ions are selected specifically.

Thus, the biological adhesive advantageously comprises fibrinogen in a content comprised between 60 and 120 mg/mL, more preferably from 80 to 100 mg/mL. Such a fibrinogen content in the adhesive provides at least one also effective adhesive bonding, of damaged tissues for example, which is notably expressed by a tearing resistance of the adhesive bonding at least as satisfactory as the two-component adhesives of the prior art, such as larger than or equal to 125 g/cm$^2$.

It comprises in particular from 50 to 500 IU/mL, more preferably from 70 to 300 IU/mL, especially between 80 and 120 IU/mL of factor VIIa and between 4 and 30 μmol/mL, more preferably between 8 and 20 μmol/mL of the calcium ion source.

In particular, the factor XIII is present in an amount from 30 IU/mL to 700 IU/mL, preferably from 100 IU/mL to 400 IU/mL.

The concentrations and activities are per milliliter of final liquid biological adhesive solution. Such a solution may notably be obtained by reconstitution of freeze-dried components. As indicated above, these plasma factors preferably present in such concentrations provide the sought functionalities for the present biological adhesive.

Sources of calcium ions represent water-soluble components, compatible with clinical use; preferably these components are inorganic salts, such as calcium chloride ($CaCl_2$) or calcium gluconate.

As indicated above, the biological adhesive of the invention is ready for use and comprises a homogenous mixture of all the components in liquid form. It may also appear in frozen form, which makes it suitable for extended storage in this form for at least 2 years without any risk of formation of fibrin, which might be observed after unfreezing. Simple resetting to room temperature is sufficient so that the adhesive may be used.

The invention also relates to a thrombin-free fibrinogen-based biological adhesive for therapeutic use, comprising the factor VIIa and a source of calcium ions, as defined earlier, appearing in a freeze-dried form, suitable for extended storage. It may be obtained by applying known freeze-drying techniques for the adhesive in the liquid form. The availability of such a presentation of the adhesive has the decisive advantage of only requiring simple reconstitution of the freeze-dried product comprising both active ingredients and the source of calcium ions in a biologically compatible solvent or aqueous medium in order to obtain the stable liquid adhesive, this preparation being carried out beforehand anticipating its use. Further, such a freeze-dried adhesive may very easily be stored at room temperature for at least 2 years without any risk of formation of fibrin, which might be observed after reconstitution. It may easily be transported right up to a site where a patient requires use of this adhesive.

The invention also relates to a kit for preparing the biological adhesive according to the invention comprising packaging means comprising a batch of freeze-dried fibrinogen plasmatic factor, a batch of freeze-dried FVIIa plasmatic factor, a batch of calcium ions source as a powder and an aqueous solvent.

Such a kit notably comprises three different individual batches in dry form, each in particular comprising one of the constitutive components of the adhesive of the invention, and in fact it is an intermediate product from which it will be then easy to merge and dissolve the batches in a biologically compatible solvent or aqueous medium, such as injectable purified water (PPI), for obtaining the stable liquid biological adhesive of the invention, if need be, concentrated, which may then be frozen. The advantage of making such a kit available is the possibility of extended storage of the three batches of different components for at least 2 years at room temperature, without observing formation of fibrin upon reconstitution, and obtaining the stable and liquid biological adhesive by simple dissolution.

In fact, the packaging means form means with which the components of the adhesive may be in particular stored and prepared, and the adhesive may be dispensed before use. They further advantageously comprise at least one container for at least three of the different components of the adhesive, including preferably at least one for each component. Each container is intended to receive one of the components, which is then dissolved in the aqueous solvent. The containers may be flasks in various glass type materials and in biologically compatible polymers.

Preferably, the packaging means may advantageously be a single container containing at least three components. Such a packaging has the advantage that a simple dissolution of the whole directly provides the liquid adhesive ready for use.

Advantageously, the kit also comprises a device for dispensing the liquid adhesive once it is prepared by dissolving the above batches with the aqueous solvent. Such a device for example represents a syringe of a suitable volume, depending on the dose of adhesive to be delivered, including a fine needle, typically of a diameter less than 2 mm, in particular less than 1 mm, or else a conventional catheter.

Preferably, the above kit includes a two-component batch from a mixture of the batches of said freeze-dried plasma factors, and the calcium ion source batch as a powder. This kit therefore comprises a batch of a freeze-dried mixture of the fibrinogen and FVIIa plasmatic factors of the invention on the one hand, and a batch of the calcium ion source as a powder on the other hand, capable of also being in the form of a freeze-dried product, for which it will be simply sufficient to merge them together and mix them up with an aqueous medium such as PPI water, before use. Alternatively, the kit may comprise a batch of a freeze-dried mixture of plasmatic factors, and a calcium ion source batch as an aqueous solution on the other hand.

Preferably, the kit of the invention is characterized by the fact that each freeze-dried fibrinogen or FVIIa plasma factor batch or the two-component batch of the mixture of said batches of freeze-dried plasma factors comprises constituents of a pharmaceutically acceptable freeze-drying stabilizing formulation. The same applies to the freeze-dried biological adhesive.

Indeed, the different freeze-dried products of the plasmatic factors are obtained by freeze-drying liquid concentrates or solutions of the plasmatic factors or each of these factors, according to conventionally applied techniques, advantageously comprising for this purpose, a freeze-drying stabilizing formulation as described in Patent Application FR 04 02001 filed by the Applicant. In this case, the stabilizing formulation advantageously represents a mixture of arginine, at least one hydrophobic amino acid and trisodium citrate and may further be added with glycine and/or lysine. Advantageously, the concentration of each of the additives per liter of protein concentrate is the following:

arginine from 25 to 50 g/L and preferably from 35 to 45 g/L (with reference to U.S. Pat. No. 5,399,670);
trisodium citrate, from 0.5 to about 12 g/L;
leucine, isoleucine or their mixtures from 5 to 15 g/L and preferably from 9 to 11 g/L; and
glycine and/or lysine, each from 1 to 5 g/L and preferably each from 1.5 to 2.5 g/L.

The stabilizing formulation may also, if need be, comprise stabilizing adjuvants known in the art.

Consequently, the invention also relates to the use of the kit according to the invention for preparing a liquid but possibly frozen biological adhesive, by reconstitution of the three batches of said kit in a biologically compatible aqueous solvent, if necessary followed by freezing.

The invention also relates to a biological adhesive as described earlier for use as a medicament. In the case when the adhesive is stored in a frozen form, it will be sufficient to unfreeze the latter before use. In the case of a freeze-dried adhesive, reconstitution in a biologically compatible aqueous solvent allows it to be used for the sought effects.

The biological adhesive of the invention is therefore used for preparing a medicament intended for haemostasis and/or heeling of damaged biological tissues, such as the skin or any organ capable of being surgically operated (spleen, liver, lungs, intestines, etc.), which as explained earlier, may represent cruentous tissues or haemorrhagic wounds, the bleeding of which may even be very low insofar that all the factors required for the coagulation cascade are present. The adhesive may be used in the presence of plasma for preparing a medicament intended to treat damaged tissues, for example for joining these tissues, selected from the group formed by cartilage, collagen, bone and bone powder.

Further, in the presence of plasma, it is also used for preparing a medicament intended to merge biomaterials selected from the group formed by alginates of polylactic acid. The presence of plasma is consequently required in certain cases for exogenous supply of plasma factors in order to initiate the coagulation cascade, and preferably it is compatible or autologous plasma. This supply may notably be performed within the scope of conventional surgical operations in stomatology or odontology.

The biological tissue may also stem from cultured and differentiated stem cells.

Although the adhesive of the invention is a medicament, in particular a dressing for local application, i.e. for external use on a wound or other injury as described above, it is not excluded that the medicament may also be a suitable gelatine capsule, either gastro-resistant or not, in which the biological adhesive is in a dry form, and ingested for treating digestive bleeding.

The stability of at least 24 hours of the adhesive of the invention allows it to remain fluid and therefore be able to be used for preparing a medicament intended to embolize nutritive blood vessels of a tumoral target. This may advantageously be achieved by an injection route which uses a conventional catheter right up to these tumoral targets in order to thereby "dry" the tumor.

With the adhesive, haemostasis may be provided through an endoscopic system used in microsurgery (samplings, biopsies, excision of polyps, etc.).

The fluidity of the present adhesive, notably related to its stability, makes its use possible through a fine needle, typically of a diameter less than 1 mm, in particular less than 0.5 mm, for application in surgery under a microscope, for example an ophthalmic application.

The following example illustrates the invention without however limiting its scope.

EXAMPLE 2 mL of a biological adhesive sample of the invention (sample A) is prepared, comprising fibrinogen at a concentration of 80 mg/mL, 100 IU/mL of factor VIIa and 5 µmol/mL of calcium chloride which are introduced into a single syringe.

A standard biological adhesive sample B of the prior art is also prepared, comprising a mixture B1 consisting of fibrinogen at a concentration of 80 mg/mL and containing 100 IU/mL of factor XIII on the one hand, and a mixture B2 consisting of calcium thrombin at 500 IU/mL on the other hand. The respective mixtures B1 and B2 are introduced into two distinct syringes, the ends of which are arranged so as to include a single needle thereby allowing the mixtures B1 and B2 to be merged together.

An anaesthetized rabbit is submitted to laparotomy. The liver is exposed and one proceeds with a first incision of the organ in order to cause bleeding on this section. After dabbing the excess of blood with a compress, the biological adhesive sample B is immediately applied on the incised section by simultaneous expulsion of the contents of both syringes by the single needle which allows a homogenous mixture of B1 and B2 to be prepared. The banks of the wound are kept joined for 30 seconds in order to let the biological adhesive set.

After heeling, it is observed that the obtained scar has irregularities and "lumps" of visible fibrin. These clusters are due to inhomogeneous setting, probably because of the fibrin formed before adhesion.

A second incision is performed at another location of the liver which is surgically treated in the same way as previously.

The biological adhesive sample A according to the invention, contained in a single syringe, is applied on the incised section and the banks of the wound are kept joined for 35 seconds in order to let the biological adhesive set.

After heeling, it is observed that the obtained scar has a clear line and withstands any deshience attempt. No trace of excess fibrin is visible, which shows that the excess adhesive has not coagulated in the absence of an operating wound and therefore without the presence of tissue factors.

The invention claimed is:

1. A thrombin-free, prothrombin-free, fibrinogen-based stable single-compound liquid biological adhesive for therapeutic use, consisting of a solvent and a mixture of fibrinogen, factor VIIa (FVIIa), and calcium ions.

2. The biological adhesive according to claim 1, wherein the solvent is water.

3. The biological adhesive according to claim 1, wherein the fibrinogen has a fibrinogen content between 60 and 120 mg/mL of final liquid biological adhesive solution.

4. The biological adhesive according to claim 3, wherein the fibrinogen content is from 80 to 100 mg/mL of the final liquid biological adhesive solution.

5. The biological adhesive according to claim 1, wherein the FVIIa has an activated factor VII content from 50 to 500 IU of activated factor VII per milliliter of final liquid biological adhesive solution (50-500 IU/mL).

6. The biological adhesive according to claim 5, wherein the activated factor VII content is from 70 to 300 IU/mL of activated factor VII, in particular from 80 to 120 IU/mL.

7. The biological adhesive according to claim 1, wherein the calcium ions are in a concentration comprised between 4 and 30 µmols/mL of final liquid biological adhesive solution.

8. The biological adhesive according to claim 7, wherein the calcium ions are in a concentration comprised between 8 and 20 µmols/mL.

9. The biological adhesive according to claim 1, further comprising the factor XIII.

10. The biological adhesive according to claim 9, wherein the factor XIII is present in an amount from 100 IU to 400 IU per milliliter of final liquid biological adhesive solution (100 IU/mL-400 IU/mL).

11. The biological adhesive according to claim 1, in a frozen form, suitable for extended storage.

12. The biological adhesive according to claim 1, in a freeze-dried form, suitable for extended storage.

13. The biological adhesive according to claim 12, further comprising constituents of a pharmaceutically acceptable freeze-drying stabilizing formulation, preferably representing a mixture of arginine, at least one hydrophobic amino acid and trisodium citrate.

14. A kit comprising, in a packaging means, a single container containing the thrombin-free, prothrombin-free, fibrinogen-based stable single-compound liquid biological adhesive for therapeutic use according to claim 1.

15. The kit according to claim 14, also comprising a device for dispensing the liquid adhesive.

16. A method for treating haemostasis or for healing damaged biological tissues, comprising applying the biological adhesive according to claim 1 to the damaged biological tissues.

17. The method according to claim 16 wherein the damaged biological tissues are cruentous tissues or haemorrhagic wounds.

18. The method according to claim 16 wherein the damaged biological tissues are skin or any organ capable of being surgically operated on.

19. The method according to claim 16, wherein said biological adhesive is in a dry form, as a dressing for local application or as a gelatine capsule.

20. A method for treating damaged tissues selected from the group formed by cartilage, collagen, bone and bone powder, comprising applying plasma and the biological adhesive according to claim 1 on the damaged tissues, and joining said damaged tissues.

21. A method for merging biomaterials selected from the group formed by alginates or polylactic acid, comprising applying plasma and the biological adhesive according to claim 1 on the biomaterials to be merged, and joining the biomaterials.

22. A method for embolizing nutritive blood vessels of a tumoral target, comprising injecting the biological adhesive according to claim 1 to said tumoral target.

* * * * *

UNITED STATES PATENT AND TRADEMARK OFFICE
CERTIFICATE OF CORRECTION

PATENT NO. : 8,383,104 B2
APPLICATION NO. : 12/096883
DATED : February 26, 2013
INVENTOR(S) : Abdessatar Chtourou It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 66 days.

Signed and Sealed this
First Day of September, 2015

Michelle K. Lee
*Director of the United States Patent and Trademark Office*